United States Patent [19]

Goettert

[11] 4,308,379

[45] Dec. 29, 1981

[54] ACUTANCE AGENTS FOR USE IN THERMALLY DEVELOPABLE PHOTOSENSITIVE COMPOSITIONS

[75] Inventor: Edward J. Goettert, Lake Elmo, Minn.

[73] Assignee: Minnesota Mining and Manufacturing Company, St. Paul, Minn.

[21] Appl. No.: 209,732

[22] Filed: Nov. 24, 1980

Related U.S. Application Data

[62] Division of Ser. No. 150,403, May 15, 1980, Pat. No. 4,271,263.

[51] Int. Cl.³ .......................................... C07D 209/12
[52] U.S. Cl. ...................................... 542/457; 430/522
[58] Field of Search ......................................... 542/457

[56] References Cited

U.S. PATENT DOCUMENTS

| | | | |
|---|---|---|---|
| 2,541,472 | 2/1951 | Kendall | 95/7 |
| 2,953,561 | 9/1960 | Doorenbos | 542/457 |
| 3,152,904 | 10/1964 | Sorensen | 96/76 |
| 3,457,075 | 7/1969 | Morgan et al. | 96/67 |
| 3,745,009 | 7/1973 | Jenkins et al. | 96/84 R |
| 3,769,019 | 10/1973 | Wiese et al. | 96/84 R |
| 3,984,248 | 10/1976 | Sturmer | 96/87 R |
| 3,988,154 | 10/1976 | Sturmer | 96/48 R |
| 3,988,156 | 10/1976 | Sturmer | 96/84 R |
| 4,033,948 | 7/1977 | Brown | 96/101 |

OTHER PUBLICATIONS

Tewari et al., Indian J. Chem. 14B (1976) pp. 419–421.

*Primary Examiner*—Arthur P. Demers
*Attorney, Agent, or Firm*—Cruzan Alexander; Donald M. Sell; Lorraine R. Sherman

[57] ABSTRACT

Acutance agents for use in thermally developable photosensitive compositions are disclosed. These novel compositions absorb scattered light and are rendered colorless at the development temperature of the photothermographic composition.

7 Claims, No Drawings

ACUTANCE AGENTS FOR USE IN THERMALLY DEVELOPABLE PHOTOSENSITIVE COMPOSITIONS

This is a division of application Ser. No. 150,403, filed May 15, 1980, now U.S. Pat. No. 4,271,263.

TECHNICAL FIELD

This invention relates to compounds suitable for use as acutance dyes in photosensitive compositions, to the preparation of such compounds and to photosensitive compositions containing the compounds. The invention is particularly concerned with thermally developable photosensitive compositions of the type known as "dry silver" photothermographic compositions.

BACKGROUND ART

Dry silver photosensitive or photothermographic compositions comprise an intimate mixture of a light-sensitive silver halide and another silver compound such as a silver salt of an organic acid, e.g. silver behenate or silver saccharine, which upon reduction gives a visible change and which is substantially light-insensitive. Such a mixture is usually prepared in suspension and the resulting dispersion spread as a layer on a suitable substrate to produce, for example, a sheet material. When dry, the layer is exposed to a light image and thereafter a reproduction of the image can be developed by heating the layer in the presence of a reducing agent for silver ions such as hydroquinone or certain substituted phenols.

It is because the exposure and development of the layer occur without using water, that these materials are often referred to as dry silver light-sensitive materials. Such materials, in which minor amounts of a photosensitive silver halide catalyst-progenitor are associated in catalytic proximity with major amounts of a heat sensitive oxidation-reduction image forming reaction mixture which mixture reacts more rapidly in the presence of the catalyst (silver) resulting upon exposure of the silver halide, are well known in the art.

It is believed that when the mixture is exposed to light a latent image is formed in the silver halide. Thereafter, the silver compound can be reduced by heating in the presence of the reducing agent, this reduction being catalyzed image-wise by the silver formed on the light exposed silver halide. By a suitable choice of temperature, the reduction of the silver compound can be catalyzed in the light exposed areas to give a visible darkening while any slight reduction which occurs in the non-light exposed areas is insufficient to give a marked visible change. Because the silver halide acts as a catalyst progenitor, very small amounts of it can suffice, e.g. 0.1 to 10% by weight of the mixture. However, large amounts, e.g. up to 15 or even 20% may be desirable in some circumstances.

In order to improve the sharpness or definition of photographic images a dye known as an acutance dye is often incorporated into photo-sensitive compositions. To be effective, the acutance dye will absorb at the wavelengths at which the photosensitive composition is sensitive. The longer the path length of the light in the layer of light-sensitive composition, the greater the attenuation. Therefore, scattered light is attenuated or absorbed to a larger extent than light which impinges directly on a light-sensitive crystal. As a result, although the overall speed of the composition is reduced slightly, scattered light and other light rays which are liable to produce a blurred image are preferentially absorbed and so the overall definition and sharpness of images produced in the layer are increased.

An acutance dye for use in a dry silver composition is preferably heat labile in the system, that is to say, it is destroyed by the heat development of the photothermographic composition to one or more compounds which are substantially colorless. The exact mechanism of this reaction is not known.

The thermal development process described above and sometimes known as the "dry silver" process is disclosed, for example, in U.S. Pat. Nos. 3,152,904 and 3,457,075.

Acutance agents for use in thermally-developable photographic materials have been described. In U.S. Pat. No. 3,745,009 there are described antihalation compounds which are energy-decolorizable and suitable for use in thermally-developable photographic materials but are, however, excessively sensitive to heat during production and coating and may decompose prematurely due to ambient heat.

In U.S. Pat. No. 3,769,019 there are disclosed acutance agents which are thermally-decolorizable protonic dyes although color may return spontaneously after a period of time.

In U.S. Pat. Nos. 3,984,248, 3,988,154 and 3,988,156 there are disclosed thermally stable, photobleachable o-nitro-substituted arylidene dyestuffs of the general formula:

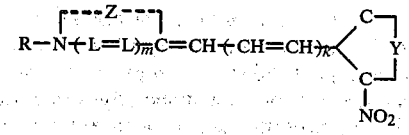

wherein k=0, 1 or 2; m=0 or 1; L is a methine or substituted methine group; R is an alkyl, substituted alkyl, alkenyl, aryl or substituted aryl group; Y represents the atoms necessary to complete a mono- or polycyclic aryl group which may be further substituted; and Z represents the atoms necessary to complete a mono- or polycyclic heterocyclic nucleus which may be substituted, the heterocyclic ring containing the nitrogen atom shown being 5 or 6 membered. These dyestuffs may be incorporated in heat developable photographic elements as part of an antihalation layer. Such elements may be exposed to a light pattern, thermally developed to provide a sharp image in the element, and then the element fully exposed to light to decolorize the antihalation compounds. Alternatively the compounds may be incorporated as desensitizers in photosensitive compositions for wet processing. Patentee's compounds have an odd number of carbon atoms in the methine bridging group between the cyclic units. This differs from the 2-membered methine chain of the compounds of the present invention. In addition, patentee's compounds do not include the indole nucleus as the heterocyclic moiety. Patentee's compounds are made by reaction of a heterocyclic salt and a nitrosubstituted compound. Such a preparation will not lead to the compounds of the present invention.

Certain nitrostyryl dyes are known to act as desensitizing dyes. In U.S. Pat. Nos. 2,953,561 and 3,023,102 styryl dye bases are utilized as desensitizers for the production of direct positive photographic emulsions. These dye bases are of the general formula:

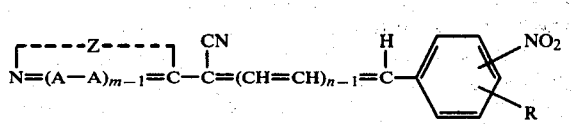

wherein R is hydrogen, halogen, hydroxy, amino, nitro, etc.; n is an integer of from 1 to 2; m is an integer of from 1 to 2; A is a methine group and Z represents the non-metallic atoms necessary to complete a heterocyclic nucleus containing 5 to 6 atoms in the ring. Patentee's compounds can include an indolenine nucleus rather than an indole nucleus such as in compounds of the present invention.

In U.S. Pat. No. 2,541,472, styryl bases in which the nitrogen atom is quaternized are used as desensitizing dyes.

U.S. Pat. No. 4,033,948 discloses certain members of the class of odd-numbered methine arylidene dye bases useful as acutance agents in thermally-developable photosensitive compositions.

Assignee's three copending applications, Ser. No. 964,479 (Lea and Reece), Ser. No. 964,480 (Brown), both filed Nov. 29, 1978, and Ser. No. 98,386 (Lea and Burrows), filed Nov. 29, 1979, likewise disclose acutance agents for use in thermally developable photosensitive compositions.

One aspect of this invention provides dry silver compositions containing acutance dyes, which absorb light in at least some of those wavelengths to which the composition is sensitive and which are rendered colorless upon heat development of the dry silver composition.

In another aspect the invention provides novel compounds suitable for use as acutance dyes in photothermographic compositions such as in sheet materials, and a method for their preparation.

In still another aspect of this invention acutance agents for use in dry processing silver reproduction materials are provided, particularly acutance agents which do not tend to desensitize the photosensitive compounds in said reproduction materials.

DISCLOSURE OF INVENTION

According to the invention there are provided storage stable, light-sensitive compositions comprising an intimate mixture of a substantially light-insensitive silver compound which upon reduction gives a visible change and sufficient quantity of a silver halide to catalyze said reduction to give a visible change in those areas where the silver halide has been exposed to light and when the intimate mixture is heated in the presence of a reducing agent for silver ion, the intimate mixture including as an acutance dye a styryl dye compound. The acutance agents of the invention do not desensitize thermally-developable photosensitive compositions in the 350 nm region of the spectrum.

It is found that dry silver compositions containing the above noted acutance dyes can give excellent sharp images and that the acutance dye will be rendered essentially colorless by the heating required to develop the composition. This is unexpected in view of the fact that many of these dyes are found not to be decomposed to a colorless state when they are heated on their own to the temperature at which the dry silver compositions are heated for development.

The acutance dyes can be incorporated into the dry silver compositions of the invention in concentrations of about 0.01 to about 0.1 parts by weight (0.3 to 3.0 micromoles) of acutance agent (having a molecular weight of about 300) per 100 parts by weight of photosensitive dispersion. The use of more acutance agent in coating an emulsion produces an increase in fog level and increase in residual stain. Lesser amounts are generally found to be ineffective. Preferably about 0.02 to 0.05 parts (0.5 to 1.5 micromoles), and more preferably, about 0.02 to 0.035 parts (0.5 to 1.2 micromoles) of acutance agent having a molecular weight of about 300 is used per 100 parts of photosensitive dispersion. Amounts expressed as micromoles are applicable to acutance agents of the invention in general.

The light-sensitive compositions of the invention will normally be spread for use on a support producing, for example, thermally curable photosensitive sheet materials. Suitable supports include, for example, paper, polyester or polyamide film bases, and glass. The composition will normally be prepared as a solution or suspension which is spread as a layer on the support and then the solvent or vehicle is evaporated to leave a dry photosensitive layer. If desired, a coating aid or binder such as polyvinyl butyral, polymethyl methacrylate, cellulose acetate, polyvinyl acetate, cellulose acetate propionate and cellulose acetate butyrate, can be incorporated in the light-sensitive mixture.

The substantially light-insensitive silver compound is a silver salt of an organic acid or a complex of silver salts. The silver source materials are preferably selected from silver salts of long chain fatty acids (i.e. $C_{12}$ to $C_{30}$ carboxylic or polycarboxylic acids, most preferably $C_{16}$ to $C_{26}$ carboxylic acids), for example, silver behenate, silver laurate, silver myristate, silver palmitate, silver stearate and mixtures of these acids. Other silver salts of organic acids include silver arachidate and silver saccharine. Either a pure single acid salt or salt from a mixture of acids may be used. Also preferable are complexes of silver salts wherein the coordinating compound has a gross stability constant of between 4.50 and 10.0 for silver ion.

The reducing agent for this substantially light-insensitive silver compound can normally be quite mild. Suitable examples include hydroquinone and substituted phenols such as 1-methyl-4-hydroxynaphthalene, methyl gallate, catechol, phenylene diamine, p-aminophenol and 1-phenyl-3-pyrazolidone. The reducing agent can be incorporated into the light-sensitive composition. Alternatively, the composition can be placed in contact with the reducing agent after exposure to light. For example, a light-sensitive coating can be exposed to a light image, placed in contact with a layer containing the reducing agent and the image then developed by heating. Preferably, however, the reducing agent is incorporated in the light-sensitive composition before this is spread on the support. The storage stability of the composition can be improved by incorporating in the composition a small amount of an acid stabilizer, such as succinic acid, benzoic acid or salicyclic acid.

The silver halide can be present in amounts of up to 20% by weight of the mixture of silver compounds or can be present in small amounts, e.g., 0.1 to 10% by weight of the mixture of silver compounds. It can be added as such to the substantially light-insensitive compound or formed in situ by adding a soluble halide, e.g., a mercury or sodium halide, to the substantially light-insensitive silver compound. The silver halide can, for example, be chloride, bromide or a mixture of them and/or other silver halides.

DETAILED DESCRIPTION OF THE INVENTION

According to the invention there are provided light-sensitive compositions comprising an intimate mixture of a substantially light-insensitive silver compound which upon reduction gives a visible change and sufficient quantity of a silver halide to catalyze said reduction to give a visible change in those areas where the silver halide has been exposed to light when the intimate mixture is heated in the presence of a reducing agent for silver ion, the intimate mixture including as an acutance dye a compound of the general formula:

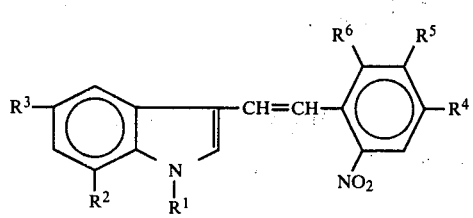

wherein:

$R^1$ represents hydrogen, an alkyl group of 1 to 18 carbon atoms or an aryl group of 6 to 10 carbon atoms, the alkyl or aryl group optionally substituted by halogen, by an alkoxy group of 1 to 6 carbon atoms or by an aryl group of 6 to 10 carbon atoms; and preferably $R^1$ is hydrogen;

$R^2$ and $R^3$ independently represent hydrogen, an alkyl group of 1 to 6 carbon atoms, an alkoxy group of 1 to 6 carbon atoms, or halogen;

$R^4$ represents hydrogen, nitro, cyano, a carbalkoxy group of 1 to 6 carbon atoms, or halogen; and preferably $R^4$ is a nitro group;

$R^5$ is hydrogen;

$R^6$ represents hydrogen, nitro, cyano, a carbalkoxy group of 1 to 6 carbon atoms, or halogen; or $R^5$ and $R^6$ together constitute a benzo group.

The acutance agents used in the compositions of the invention are styryl dyes that contain an indole nucleus and are further substituted on the aryl group by a nitro group in the ortho position and they can be prepared by processes which are well known.

An appropriately substituted toluene derivative of Formula II,

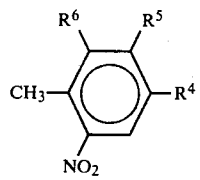

wherein $R^4$, $R^5$ and $R^6$ are defined as above are reacted in a base catalyzed condensation reaction with a heterocyclic aldehyde of Formula III:

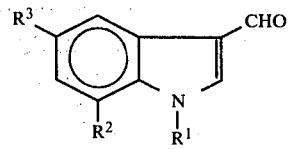

wherein $R^1$, $R^2$ and $R^3$ are defined above. Generally, the reaction is carried out in the absence of solvent. Alternatively, additional base may serve as the reaction solvent or aprotic solvents such as acetonitrile or dimethylformamide may be used. The reaction mixtures are heated on a steam bath for a time period ranging from a few hours to a few days. The product may then be isolated by well known procedures, i.e., crystallization or removal of solvent and purified by recrystallization.

Examples of acutance agents of the invention are the compounds and their correspondingly numbered structural formulae in Table I. The following Formula IV illustrates the numbering system utilized in the naming of these compounds with the positional number in parenthesis.

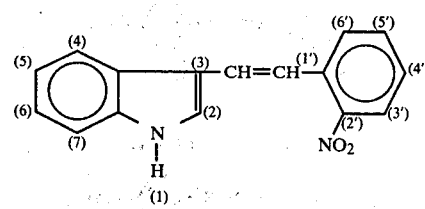

It can be seen that the acutance dyes of the invention are based on an indole nucleus. The aryl group is substituted in the ortho position by a nitro group and the aryl group connects to the heterocyclic unit by a two-membered methine chain.

TABLE I

| | Acutance Dyes and Corresponding Formulae |
|---|---|
| 1. | 3-(2',6'-dinitrostyryl)-1(H)-indole |
| 2. | 5-bromo-3-(2',6'-dinitrostyryl)-1(H)-indole |
| 3. | 3-(2'-carbomethoxy-4',6'-dinitrostyryl)-1(H)-indole |
| 4. | 3-(4'-carbomethoxy-2',6'-dinitrostyryl)-1(H)-indole |
| 5. | 5-methyl-3-(2',4'-dinitrostyryl)-1(H)-indole |
| 6. | 5-methoxy-3-(2'-carbomethoxy-4',6'-dinitrostyryl)-1(H)-indole |
| 7. | 3-(2',4'-dinitrostyryl)-1(H)-indole |
| 8. | 3-(2'-nitrostyryl)-1(H)-indole |
| 9. | 1-benzyl-3-(2',4'-dinitrostyryl)-1(H)-indole |
| 10. | 3-(4'-cyano-2'-nitrostyryl)-1(H)-indole |
| 11. | 7-methyl-3(2',6'-dinitrostyryl)-1(H)-indole |
| 12. | 3-(4'-chloro-2'-nitrostyryl)-1(H)-indole |
| 13. | 3-(2'-chloro-6'-nitrostyryl)-1(H)-indole |
| 14. | 3-(2'-carbomethoxy-6'-nitrostyryl)-1(H)-indole |
| 15. | 3-(4'-carbomethoxy-2'nitrostyryl)-1(H)-indole |
| 16. | 3-[2-(2'-nitro-1-naphthyl)-ethenyl]-1(H)-indole |
| 17. | 1-methyl-3-(2',4'-dinitrostyryl)-1(H)-indole |
| 18. | 1-methyl-3-(2'-cyano-6'-nitrostyryl)-1(H)-indole |
| 19. | 3-(2',4',6'-trinitrostyryl)-1(H)-indole |
| 20. | 5-bromo-3-(2',4'-dinitrostyryl)-1(H)-indole |
| 21. | 1-octadecyl-3-(2',4'-dinitrostyryl)-1(H)-indole |
| 22. | 1-(2-chloroethyl)-3-2'-4'-dinitrostyryl-1(H)-indole |
| 23. | 3-(2'-nitrostyryl-1(4-chlorophenyl)-indole |
| 24. | 3-(2'-nitrostyryl)-1(4-methoxyphenyl)-indole |

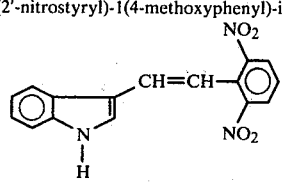

1.

TABLE I-continued
Acutance Dyes and Corresponding Formulae
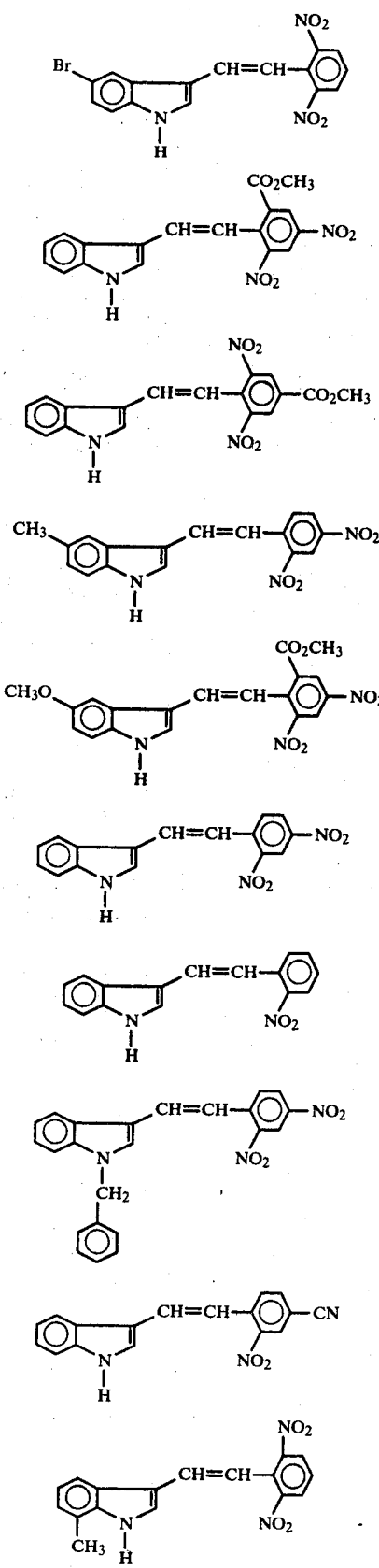
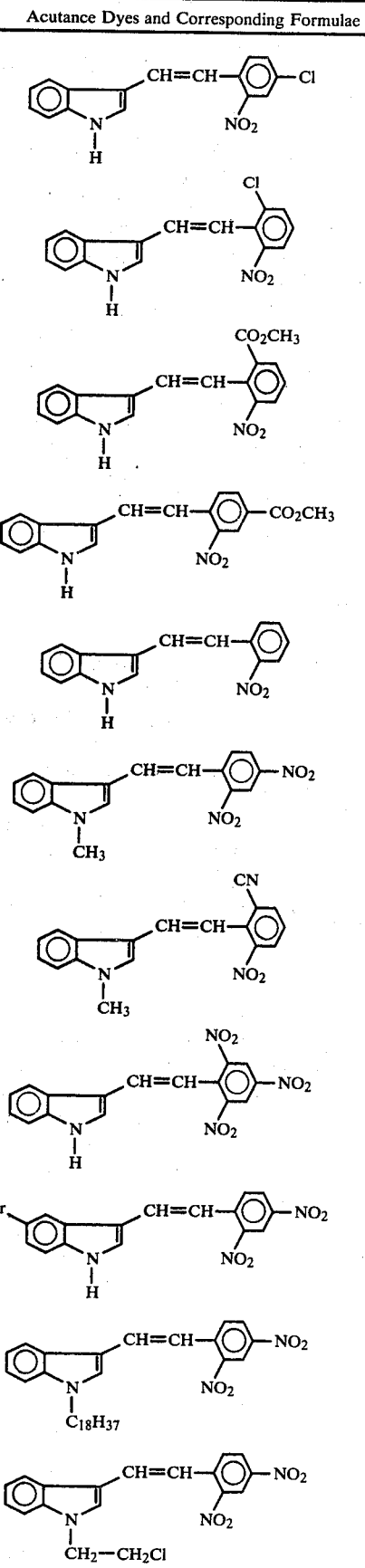

TABLE I-continued
Acutance Dyes and Corresponding Formulae

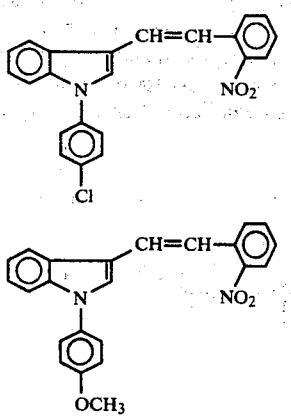

23.

24.

The invention is now further explained by the following non-limiting examples showing the preparation and use of the acutance agents of this invention.

EXAMPLE 1
Preparation of 3-(2',4'-dinitrostyryl)-1(H)-indole (Number 7 of Table I)

Indole-3-carboxaldehyde (14.5 g, 0.1 mole) and 2,4-dinitrotoluene (18.2 g, 0.1 mole) were combined in a flask along with a catalytic amount of piperidine (0.5 ml) and heated on a steam bath. During the course of the heating, the reaction mixture went from solid to liquid and back to solid. After resolidification, the mixture was heated an additional two hours on the steam bath. After recrystallization of the crude product from an ethyl acetate/hexane mixture, orange crystals were obtained with infrared absorption spectra (IR) and nuclear magnetic resonance spectra (NMR) that were consistent with the proposed structure of Number 7. The NMR spectrum shows the 3', 5' and 6' protons at 1.27, 1.58 and 1.70 respectively with the splitting pattern expected of the dinitro ring. The vinylene group is an AB pattern at 2.06 and 2.50, and the indole ring has the 1-H at −1.76, the 2-H at 2.10 and complex patterns for the 4-H at 2.05, the 5 and 6-H at 2.75, and the 7-H at 2.45. Peak matching in the high resolution spectra (MS) gave the value 309.0725 for the parent iron, which corresponds well to the formula $C_{16}H_{11}N_3O_4$ as proposed.

EXAMPLE 2
Preparation of 5-methyl-3-(2',4'-dinitrostyryl)-1(H)-indole (Number 5 of Table I)

5-methylindole-3-carboxaldehyde (0.159 g, 0.001 mole) and 2,4-dinitrotoluene (0.182 g, 0.001 mole) were combined with three drops of piperidine as in Example 1 to give orange-brown crystals whose IR spectrum is consistent with the structure of Number 5. NMR peaks ($\tau$ units in parts per million) were found as noted: 1H (−1.64), 2H (2.14), 4H (2.26), 6H (2.92), 7H (2.62), 3'H (1.28), 5'H (1.59), 6'H (1.70) with the vinylene group having an AB pattern at 2.07 and 2.52 and the methyl group appearing at 7.53. Parent ion determined by peak matching from the high resolution mass spectrum is 323.0894 corresponding to the formula $C_{17}H_{13}N_3O_4$ of the proposed structure.

The synthetic procedure similar to that of Example 1 was followed for compounds of Examples 3 through 7 using appropriate starting materials. The spectral data obtained appears after the compound.

EXAMPLE 3
Preparation of 1-benzyl-3-(2',4'-dinitrostyryl)-1(H)-indole (Number 9 of Table I)

IR: Consistent for proposed structure.

NMR ($\tau$ units in parts per million): 2H (1.94), 4H (2.04), 5H and 6H (2.75), 7H (2.42), 3'H (1.25), 5'H (1.58), 6'H (1.67) with the vinylene groups having an AB pattern at 2.06 and 2.49 and the benzyl group on the N has the CH$_2$ at 4.49 and aromatic protons at 2.71.

MS: Parent ion at 399.1189 corresponding to the formula $C_{23}H_{17}N_3O_4$ of the proposed structure.

EXAMPLE 4
Preparation of 5-bromo-3-(2',4'-dinitrostyryl)-1(H)-indole (Number 20 of Table I)

IR: Consistent for proposed structure.

NMR ($\tau$ units in parts per million): 1H (−1.92), 2H (2.02), 4H (1.84), 6H and 7H (overlapping from 2.4–2.7), 3' (1.29), 5' (1.58), 6' (1.67) with the vinylene group having an AB pattern at 2.07 and 2.56.

MS: Parent ion at 386.9838 corresponding to the formula $C_{16}H_{10}BrN_3O_4$ of the proposed structure.

EXAMPLE 5
Preparation of 3-(2'-carbomethoxy-4',6'-dinitrostyryl)-1(H)-indole (Number 3 of Table I)

MS: Parent ion at 367.0807 corresponding to the formula $C_{18}H_{13}N_3O_6$ of the proposed structure.

EXAMPLE 6
Preparation of 3-(4'-chloro-2'-nitrostyryl)-1(H)-indole (Number 12 of Table I)

MS: Parent ion at 298.0499 corresponding to the formula $C_{16}H_{11}ClN_2O_2$ of the proposed structure.

EXAMPLE 7
Preparation of 3-[2-(2'-nitro-1-naphthyl)-ethenyl]-1(H)-indole (Number 16 of Table I)

MS: Parent ion at 314.1047 corresponding to the formula $C_{20}H_{14}N_2O_2$ of the proposed structure.

EXAMPLES 8–12

Under room light, a 1000 gram dispersion containing 12.5 parts of silver behenate in 87.5 parts of solvent comprising of 75 parts methyl ethyl ketone and 25 parts toluene was charged to a mixing vessel maintained at 15° C. Twenty grams of polyvinyl butyral resin and 10 grams of 1-methyl-2-pyrrolidinone were added, and the mixture stirred. After 30 minutes, under a Wratten 1A safelight, a mixture containing hydrobromic acid (15 ml, 2.0 molar in ethanol) and hydroiodic acid (7 ml, 0.1 molar in ethanol) was pipetted in with stirring. After 30 minutes an additional 60 grams of polyvinyl butyral in solvent were charged, followed in 20 minutes by mercuric bromide (4 ml, 0.5 molar in ethanol) and in five minutes by 15 grams of 2,6-bis(2'-hydroxy-3'-tert-butyl-5'-methylbenzyl)-4-methylphenol and 10 grams of phthalazinone. After 20 minutes 12 grams of a solution containing 2 mg of compound Formula V per gram 1-methyl-2-pyrrolidinone was added, and the mixture was stirred an additional 30 minutes.

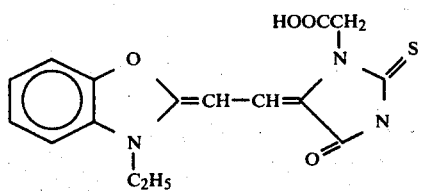

Equimolar amounts of four acutance dyes at two different concentrations A and B to be tested were added to appropriate containers and dispersed in 3 ml methyl ethyl ketone. Fifty gram portions of the light-sensitive dispersion prepared above were then added to each container, thoroughly mixed and knife coated 100 microns thick on polyester film. Each coating sample so prepared was dried 3.5–4.0 minutes at 85° C. These dried coatings were overcoated with the coating knife set 65 microns above the base using an overcoat solution containing 95 parts by weight methyl ethyl ketone and 5 parts by weight of a vinyl chloride/vinyl acetate copolymer and dried as before. For use as a control, two coatings were prepared without adding an acutance dye. Each dried coating was exposed using a combination of tungsten source narrow band filter, and an aperture target overlaid with a 0 to 4 continuous density wedge in a vacuum frame to make contact exposures at a wavelength closely matching the spectral absorbance maximum of each dye. Microdensitometer traces across the width of the image at D=1.5 (obtained after processing the exposed strips 20 seconds at 127° C. in a fluorochemical bath to give reproducible heating for these tests) were used to judge the effectiveness of each dye. The widths reported are in centimeters as obtained from the density profile of each image on the microdensitometer chart. The results of the tests are given in Table II.

It can be seen by reference to Table II that the flare factor of photosensitive emulsion coatings is reduced from a minimum of 1.03 to 1.19 for coatings not containing the acutance dyes of the invention to a value ranging from 0.35 to 0.87 depending on the particular acutance dye and its concentration used in the emulsion coatings.

The lower numbers for the width at the base of the density profiles indicate a reduction of flare in the image.

What is claimed is:

1. A compound which has a maximum absorption of visible light between 440 and 460 nm and which provides a flare factor of less than 0.9 to photosensitive emulsion coatings said compound having the general formula:

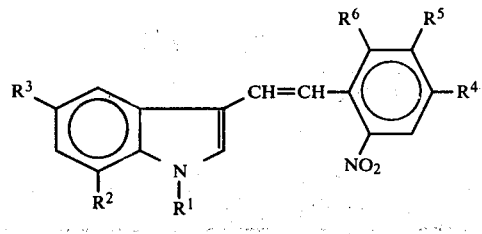

wherein:
$R^1$ represents hydrogen, an alkyl group of 1 to 18 carbon atoms or an aryl group of 6 to 10 carbon atoms, the alkyl or aryl group optionally substituted by halogen, by an alkoxy group of 1 to 6 carbon atoms or by an aryl group of 6 to 10 carbon atoms;

$R^2$ and $R^3$ independently represent hydrogen, an alkyl group having 1 to 6 carbon atoms, an alkoxy group having 1 to 6 carbon atoms, or halogen;

$R^4$ and $R^6$ independently represents hydrogen, nitro, cyano, a carbalkoxy group having 1 to 6 carbon atoms, or halogen, and at least one of $R^4$ and $R^6$ is a nitro, cyano, carbalkoxy group having 1 to 6 carbon atoms, or halogen;

$R^5$ is hydrogen;

or $R^5$ and $R^6$ together constitute a benzo group.

2. A compound according to claim 1 wherein $R^1$ is hydrogen.

3. A compound according to claim 1 wherein $R^4$ is a nitro group.

4. A compound, 3-(2',4'-dinitrosytryl)-1(H)-indole, according to claim 1.

5. A compound, 1-benzyl-3-(2',4'-dinitrostyryl)-1(H)-indole, according to claim 1.

6. A compound, 5-bromo-3-(2',4'-dinitrostyryl)-1(H)-indole, according to claim 1.

7. A compound, 5-methyl-3-(2',4'-dinitrostyryl)-1(H)-indole, according to claim 1.

* * * * *

TABLE II

| | | | Density Profile Data | | | Acutance Test Microdensitometer Traces (cm) | | Flare |
|---|---|---|---|---|---|---|---|---|
| Ex. No. | Dye (Figure) | Conc. mg/50 | $D_{min}$ Vis. | UV | nm | ½ width at ½ height(a) | ½ width at ½ base (b) | Factor b-a/a |
| 8A | Control | — | .10 | .25 | 440 | 3.45 | 7.55 | 1.19 |
| 8B | Control | — | .09 | .24 | 460 | 3.55 | 7.20 | 1.03 |
| 9A | 5 | 5.2 | .08 | .23 | 440 | 3.50 | 6.30 | 0.80 |
| 9B | 5 | 10.4 | .12 | .26 | 440 | 3.55 | 5.35 | 0.51 |
| 10A | 7 | 5.0 | .10 | .25 | 440 | 3.40 | 6.35 | 0.87 |
| 10B | 7 | 10.0 | .12 | .27 | 440 | 3.40 | 4.60 | 0.35 |
| 11A | 9 | 6.4 | .09 | .25 | 460 | 3.45 | 5.20 | 0.51 |
| 11B | 9 | 12.8 | .09 | .24 | 460 | 3.42 | 5.15 | 0.51 |
| 12A | 20 | 6.3 | .10 | .25 | 440 | 3.52 | 6.25 | 0.78 |
| 12B | 20 | 12.6 | .10 | .26 | 440 | 3.60 | 5.45 | 0.51 |

UNITED STATES PATENT AND TRADEMARK OFFICE
CERTIFICATE OF CORRECTION

PATENT NO. : 4,308,379
DATED : December 29, 1981
INVENTOR(S) : Goettert, Edward J.

It is certified that error appears in the above—identified patent and that said Letters Patent is hereby corrected as shown below:

Column 11, line 5, correct the formula to read --

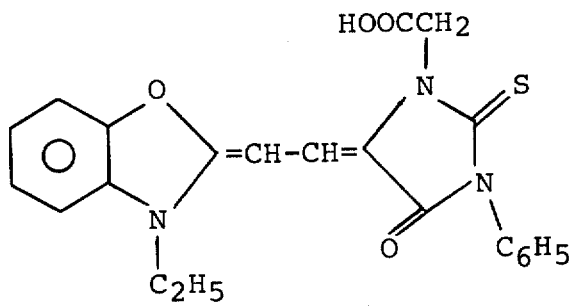

Signed and Sealed this

Fourth Day of May 1982

[SEAL]

Attest:

GERALD J. MOSSINGHOFF

Attesting Officer

Commissioner of Patents and Trademarks